United States Patent [19]

Cotell et al.

[11] Patent Number: 5,242,706
[45] Date of Patent: Sep. 7, 1993

[54] LASER-DEPOSITED BIOCOMPATIBLE FILMS AND METHODS AND APPARATUSES FOR PRODUCING SAME

[75] Inventors: Catherine M. Cotell, Alexandria, Va.; Douglas B. Chrisey, Bowie, Md.; Kenneth S. Grabowski, Alexandria; James A. Sprague, Arlington, both of Va.

[73] Assignee: The United States of America as represented by the Secretary of the Navy, Washington, D.C.

[21] Appl. No.: 738,362

[22] Filed: Jul. 31, 1991

[51] Int. Cl.5 ............................................. A61F 2/28
[52] U.S. Cl. ................... 427/2; 427/255.2; 427/255.3; 427/533; 427/586; 427/596; 204/298.02
[58] Field of Search .................. 427/2, 53.1, 38, 255.2, 427/533, 586, 596, 255.3; 204/298.02

[56] References Cited

U.S. PATENT DOCUMENTS

| | | | |
|---|---|---|---|
| 3,557,795 | 1/1971 | Hirsch | 427/2 |
| 4,702,930 | 10/1987 | Heide et al. | 427/2 |
| 4,790,851 | 12/1988 | Suire et al. | 427/255.2 |
| 4,794,023 | 12/1988 | Shimamune et al. | 427/350 |
| 4,871,578 | 10/1989 | Adam et al. | 427/2 |
| 4,882,196 | 11/1989 | Shimamune et al. | 427/2 |
| 4,908,030 | 3/1990 | Linkow et al. | 623/16 |
| 4,911,953 | 3/1990 | Hosomuma et al. | 427/224 |
| 4,944,754 | 7/1990 | Linkow et al. | 623/16 |
| 4,950,294 | 8/1990 | Hakamatsuka | 427/2 |
| 4,970,196 | 11/1990 | Kim et al. | 427/422 |
| 4,990,163 | 2/1991 | Ducheyne et al. | 623/66 |
| 5,068,122 | 11/1991 | Kokubo et al. | 427/2 |
| 5,084,300 | 1/1992 | Zander et al. | 118/641 |
| 5,085,166 | 2/1992 | Oka et al. | 427/53.1 |

OTHER PUBLICATIONS

Barthell et al., "Ion Beam Deposition of Calcium Hydroxyapatite," Biomedical Materials and Devices, vol. 110, pp. 709-713 (1989).

Ruckenstein et al., "A Nondestructive Approach to Characterize Deposits on Various Surfaces", Journal of Colloid and Interface Science, vol. 96, No. 1, 1983, pp. 245-250.

Ducheyne et al., "Structural Analysis of Hydroxyapatite Coatings on Titanium," Biomaterials 7 (2), 1987 97-103.

Solnick-Legg, "Ion Beam and Plasma Technology for Improved Biocompatible Surfaces," MRS Bulletin, 1989, pp. 27-30.

Primary Examiner—Terry J. Owens
Assistant Examiner—Diana Dudash
Attorney, Agent, or Firm—Thomas E. McDonnell; Barry A. Edelberg

[57] ABSTRACT

Biocompatible material is deposited onto a substrate by laser deposition, for example by pulsed laser beam deposition and ion-assisted pulsed laser beam deposition. The deposition can be done at room temperature, in a variety of different atmospheres, with control over the stoichiometry, adhesion and porosity of the deposited film. Apparatus for carrying out the deposition, and articles formed by such deposition, are also described. The articles so formed are particularly useful as medical prosthesis, for example, implants.

19 Claims, 5 Drawing Sheets

LASER-DEPOSITED BIOCOMPATIBLE FILMS AND METHODS AND APPARATUSES FOR PRODUCING SAME

BACKGROUND OF THE INVENTION

1. Field of the Invention

The present invention relates to a method and an apparatus for depositing biocompatible material onto a substrate, and to articles formed thereby. More particularly, the present invention provides a method and an apparatus for using a laser to deposit thin films of biocompatible material of controlled chemical composition and crystalline structure onto a substrate to provide articles which may be used as medical, dental or orthopedic implants, other medical devices designed for short- or long-term contact with human or animal tissue, or for other applications in which a biocompatible material is required in thin film form.

2. Description of the Prior Art

Medical implant devices are being increasingly used for a variety of purposes. Because living organisms generally reject any foreign matter, such devices should appear to be of natural or nonforeign material.

The design of prosthetics or other devices to be implanted in the human body must take into consideration mechanical integrity as well as biocompatibility. A number of biocompatible ceramic compositions exist, but all lack sufficient mechanical strength for use in load-bearing applications.

It has been proposed to solve this materials problem by coating a bulk material, chosen for its mechanical strength and corrosion resistance, with a thin film of biocompatible material. Such a biocompatible coating may be inert, in which case a fibrous capsule of tissue will surround the implant over time, or it may be porous, so as to encourage the ingrowth of tissue into the pores. Alternatively, such a biocompatible coating may be resorbable, i.e., it may be designed to dissolve over time and be replaced by the natural host tissue. A fourth category of biocompatible coatings includes bioactive materials that elicit a specific biological response at the interface of the material which results in the formation of a bond between the tissues and the material.

An example of a biocompatible material is hydroxylapatite, i.e., $Ca_{10}(PO_4)_6(OH)_2$, which is the primary chemical constituent of bone. Various attempts have been made to deposit hydroxylapatite films onto metal substrates, the hydroxylapatite acting as a resorbable biocompatible coating. Amorphous hydroxylapatite and calcium phosphate materials, e.g., $\alpha$-tricalcium phosphate, $\beta$-tricalcium phosphate and tetracalcium phosphate are more resorbable than crystalline hydroxylapatite (HA).

Since the resorbability of a deposited film is a function of its local chemistry, as well as its crystal structure, a useful deposition technique for coating substrates with hydroxylapatite must allow for control of chemistry, crystallinity and morphology. Prior attempts to deposit hydroxylapatite films onto substrates have suffered from various drawbacks and limitations, as discussed below.

Plasma spraying has been used to coat both metal and ceramic substrates with hydroxylapatite films. (See Cook et al., *J. Dental Research*, vol. 65 (1986) p. 222.) A number of problems have been reported to result from the plasma-spraying process, however. Adhesion of the film to the substrates is poor, giving rise to failure of finished devices. Furthermore, plasma-spraying is a high temperature technique which is unsuitable for depositing films on substrates which may degrade at elevated temperatures. In addition, the high temperature nature of the plasma-spraying technique also tends to drive structural water from hydroxylapatite, leaving films comprising a small fraction of hydroxylapatite in a matrix of dehydrated hydroxylapatite, i.e., tricalcium phosphate (TCP).

Electrophoretic deposition has been used to deposit hydroxylapatite onto Ti-6Al-4V substrates. (See Ducheyne et al., *Biomaterials*, vol. 7 (1986) p. 97.) Adhesion of the film to the substrate is poor, and sintering at high temperatures is usually needed to provide satisfactory interfacial bonding. The high-temperature sintering tends to deplete the film of phosphorus due to the formation of Ti-P compound(s) at the substrate interface, and it tends to drive water from the hydroxylapatite.

Radio frequency magnetron sputtering deposition has been employed to deposit hydroxylapatite onto substrates. (See Ruckenstein et al., *J. Colloid and Interface Science*, vol. 96 (1983) p. 245.) However, sputtering deposition tends to drive water from the hydroxylapatite and sacrifices the crystallographic structure.

Ion Beam Sputtering has been employed to deposit hydroxylapatite on substrates, however, it generally yields films that are phosphorus-deficient and amorphous. (See Barthell et al., *Materials Research Society Symposium Proceedings*. vol. 110, (1989), p. 709 and Stevenson et al., ibid., p. 715.)

SUMMARY OF THE INVENTION

An object of the present invention is to provide techniques for depositing one or more films of one or more biocompatible materials onto a substrate, more particularly, techniques which make it possible to (1) control whether each deposited film is amorphous or crystalline (or a mixture of amorphous and crystalline), (2) control the morphology (porosity and substrate/film interface structure) of each deposited film, (3) (in the case of crystalline phases) control the ratio of phases in multicomponent systems, e.g., the ratio of HA to phosphate compounds (i.e., $\alpha$- tricalcium phosphate, $\beta$-tricalcium phosphate and tetracalcium phosphate), (4) control the stoichiometry of each film, e.g., the Ca/P ratio of each deposited HA film (the theoretical Ca/P ratio for hydroxylapatite is 1.67), (5) control the resorbability of each deposited film, and (6) control the composition, crystal structure and morphology of multilayer films comprising biocompatible materials. Another object of the present invention is to provide such a technique which provides greater flexibility in the selection of process parameters, e.g., substrate temperature at deposition. A further object of the present invention is to provide such a technique in which good adhesion between the substrate and the deposited film is achieved. A further object of the present invention is to provide such a technique which provides the capability to deposit films in a variety of gaseous environments.

The present invention is also directed to coated articles formed according to such techniques and to an apparatus for carrying out such techniques.

In accordance with the present invention, there is provided a method for depositing bioceramic material onto a substrate, the method comprising exposing biocompatible material to a laser beam at a position adjacent to a substrate such that the bioceramic material is deposited onto the substrate.

The invention may be more fully understood with reference to the accompanying drawings and the following description. The invention is not limited to the exemplary embodiments and should be recognized as contemplating all modifications within the skill of an ordinary artisan.

DETAILED DESCRIPTION OF THE INVENTION

In accordance with the present invention, there is provided a method and an apparatus for depositing biocompatible material onto a substrate by exposing the biocompatible material (target) to a laser beam at a position adjacent to the substrate. Henceforth, the phrase "laser-deposited" is used to mean striking a target with a laser beam so that material is ablated off of the target and onto the substrate.

The biocompatible material may generally comprise any suitable biocompatible material. A preferred biocompatible material is hydroxylapatite, the chemical formula of which is $Ca_{10}(PO_4)_6(OH)_2$. Other biocompatible materials which may be used include HA-like phases (i.e., calcium- and phosphorus-containing phases such as $\alpha$-tricalcium phosphate, $\beta$-tricalcium phosphate, tetracalcium phosphate), natural bone, other bioceramics, for example biologically active glasses, typically referred to as bioglasses, e.g., the compositions disclosed in U.S. Pat. Nos. 4,103,002, 4,159,358, 4,234,972, 4,478,904 and 4,775,646, the entire disclosures of which are incorporated herein by reference, fluorapatite and other biocompatible materials, e.g., polymethyl methacrylate, tetraethylene glycol dimethyl ether, and fluorocarbons. The biocompatible material may comprise a single biocompatible material or a mixture of biocompatible materials.

The biocompatible material (target) may generally be in any shape suitable for being exposed to a laser beam (for example, a pellet, disc, cylinder or sphere). The preferred condition of the biocompatible material (target) is a dense pellet. A particularly preferred pellet diameter is about 0.75 inch. In the case of biocompatible ceramics such as hydroxylapatite that are typically delivered in the form of powders suspended in buffer solutions, the powders may be dried in a vacuum oven and subsequently pressed into dense pellets. The preferred temperature range for the vacuum drying is <120° C. and the preferred range of pressures for the pressing procedure is 40,000–100,000 psi. The pellets may then be sintered preferably in $O_2$ at a temperature preferably within the range of from 450° C. to 650° C. and cooled, preferably slowly, to room temperature.

The substrate is preferably corrosion-resistant, and it may generally comprise any suitable material, e.g., metal, alloy, ceramic and/or polymer material in any suitable shape. Preferred substrates include Ti-6Al-4V, other Ti alloys, essentially pure Ti, Si, GaAs, InP, GeSi, SiC, silastic, PVC, MgO, $Al_2O_3$, stainless steels, Co-Cr alloys and synthetic rubbers such as latexes and silicone rubbers. Ti-6Al-4V is particularly preferred. The substrate is preferably mounted on a substrate holder. For depositing HA, the substrate holder is preferably electrically isolated, although for some applications, the substrate holder may be biased. The substrate can generally be of any desired shape and orientation. For instance, the shape can be regular (e.g., flat and planar, tubular) or irregular. For many applications of the present invention, the substrate is of irregular shape. The orientation can be crystallographically oriented, polycrystalline, or amorphous.

Any suitable laser source can be employed. In general, as discussed below, a short pulsed laser is particularly preferred in accordance with the present invention. For example, an excimer laser (e.g., ArF, KrF, XeF or XeCl) can be used, a KrF excimer laser being especially preferred. Other short pulsed lasers, e.g., Nd-YAG or $CO_2$, could be used.

The biocompatible material (target) being exposed to the laser beam and the substrate are preferably positioned within a chamber having an environment whose temperature, pressure and chemical composition are controlled. Suitable environments according to the present invention include argon/water, oxygen, and other reactive gas mixtures (for example, those having a partial pressure of oxygen such as carbon monoxide/carbon dioxide, hydrogen, water) as well as inert gases, such as argon. Two particularly preferred environments in accordance with the present invention are argon/water and oxygen. For creating an argon/water environment, there may be provided a gas inlet port which passes through a bubbler before passing into a vacuum chamber—for creating an oxygen environment, there may be provided a gas inlet port which passes directly into a vacuum chamber. The background pressure within the chamber during a deposition may be within the range of from about 0–760 Torr; 0.3 Torr is a particularly preferred total pressure.

The distance between the target and the substrate is preferably within the range of from about 3 cm to about 10 cm. A particularly preferred distance is about 4 cm. In general, larger distances are more suitable for depositing on larger substrate areas. Distances of greater than 10 cm may be used if desired, for example, for depositing on larger surface areas.

The thickness of the deposited film is proportional to the number of laser pulses to which the target is exposed, and may be selected depending on the purpose for which the finished article is to be used.

The biocompatible material (target) may be mounted on any support means suitable for supporting the biocompatible material. In accordance with a preferred aspect of the present invention, the biocompatible material (target) is mounted on a moving support means, such as a rotating and/or translating shaft, such that different portions of the target are in the center of the laser beam at different times, thereby extending the useful lifetime of the target and providing enhanced film uniformity. A preferred rate of rotation (and the rate employed in the Examples which follow herein) is about 0.5 revolution per second. Such an arrangement allows for greater uniformity of deposition on the substrate. Instead of (or in addition to) moving the biocompatible material (target), the center of the laser beam could be moved to achieve similar effects. In general, larger areas may be coated by rastering the center of the laser beam across the target surface. In these cases, larger targets (diameters >0.75 inch) would be preferred. In accordance with one modification according to the present invention, the substrate may be manipulated (e.g., rotated and/or translated) during deposition to allow deposition on nonplanar or irregularly-shaped substrates.

In accordance with another preferred aspect of the present invention, the laser may be a pulsating laser (as mentioned above, short pulsed lasers are preferred according to the present invention). Lasers for use in accordance with the present invention generally emit light having a wavelength in the range of from about 193 nm to about 1100 nm, an energy in the range of from about 0.1 to about 10 J/cm$^2$, a pulsewidth of from about $10^{-12}$ to about $10^{-6}$ second and a pulse repetition frequency of from about 0 to about 1000 Hz. In general, energy density (fluence) affects morphology—higher energies tend to produce deposited films which have larger particles and which are less dense. In the Examples which follow herein, there was employed a laser that emitted light having a wavelength of about 248 nm, an energy of about 250 mJ/pulse, a pulsewidth of about 30 ns and a pulse repetition frequency of about 20 Hz.

As the biocompatible material is being deposited, the substrate may be maintained at ambient temperature or may be heated to any temperature up to about 800° C. or higher. Any suitable heating means may be used for this purpose. For example, one or more radiant heaters may be positioned so as to heat the surface of the biocompatible film continuously as it is deposited on the substrate. Alternatively, the substrate holder may be heated, e.g., by a quartz lamp. As discussed below, for many applications, precise temperature control at the surface of deposition is required.

In accordance with one modification according to the present invention, the substrate may first be deposited by laser deposition (preferably pulsed) and then the biocompatible film may be deposited on the thus-formed substrate.

Figure 1:
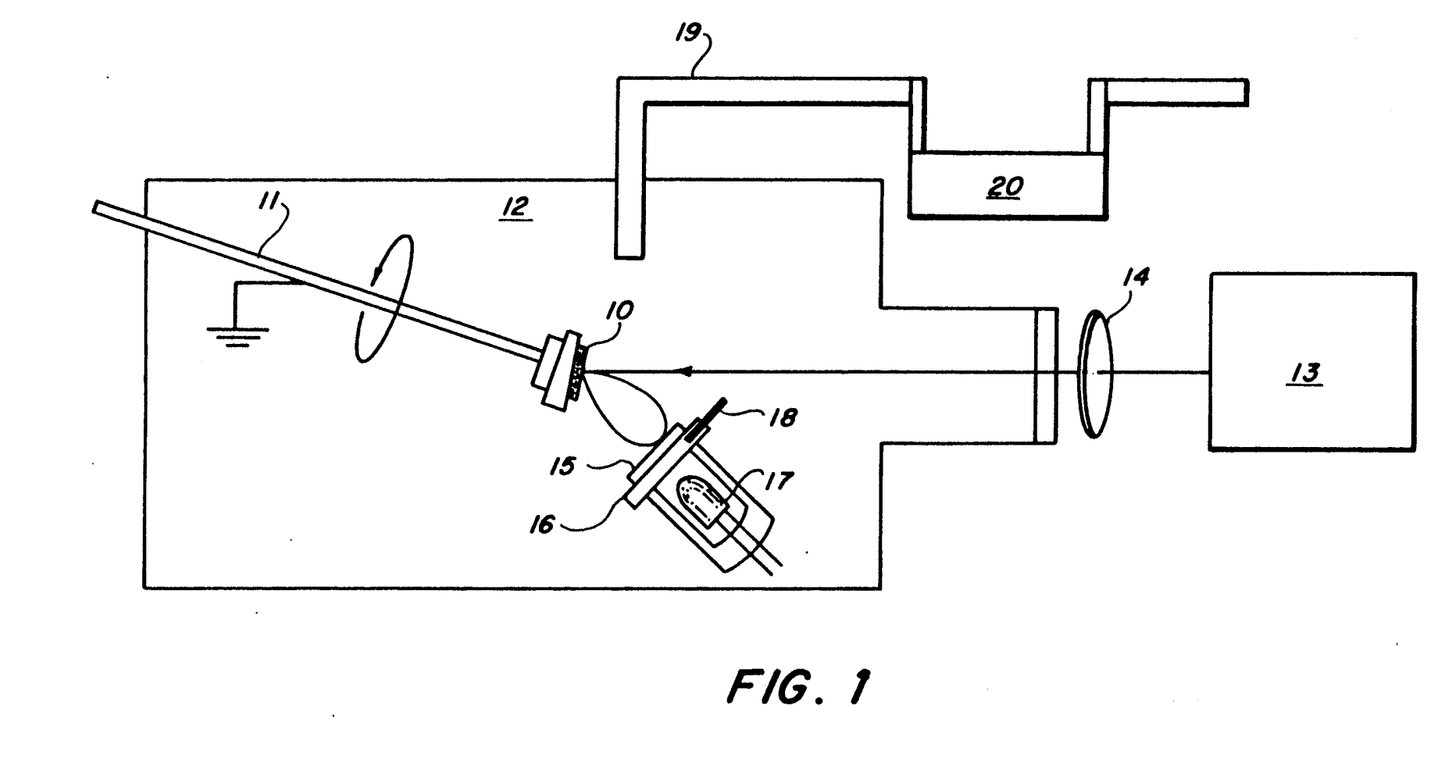
FIG. 1 is a schematic drawing depicting one embodiment in accordance with the present invention.

Referring to FIG. 1, which depicts a first system in accordance with the present invention, a pellet 10 of biocompatible material is affixed to a rotating shaft 11 positioned within a vacuum chamber 12. A laser from a laser source 13 is focused through a lens 14 onto the pellet 10. A substrate 15 is mounted on a substrate holder 16 which is heated by a quartz lamp 17. The temperature of the substrate holder is monitored by a thermocouple 18. A gas inlet port 19 allows introduction of the desired gas or gas mixture into the vacuum chamber 12. A bubbler 20 is provided in the gas line leading to the gas inlet port 19.

Figure 2:
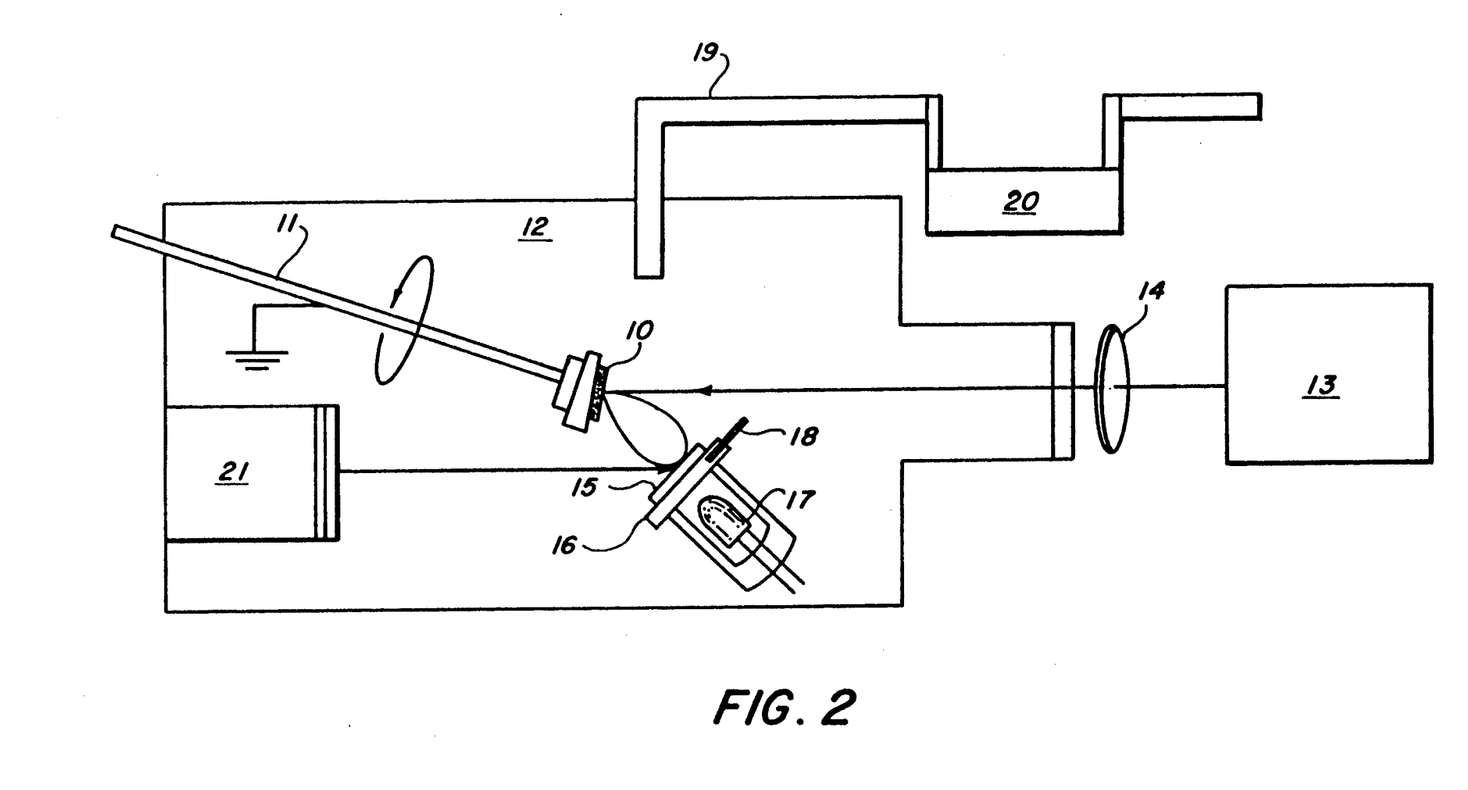
FIG. 2 is a schematic drawing depicting a second embodiment in accordance with the present invention.

A laser deposition system according to the present invention may optionally further comprise an ion source. FIG. 2 depicts a laser deposition system like the one shown in FIG. 1, which further includes a Kaufman ion source 21. A suitable ion source is a Kaufman ion source employing inert gases such as Ar+ and/or reactive gases such as O$_2$+ or CO+ operating at about 50–1500 eV. Such an ion source can be used to pre-clean substrates in situ, to improve the adhesion between the deposited film of biocompatible material and the substrate, and/or to densify the biocompatible material as it is being deposited. When employing an ion source in accordance with the present invention, the pressure in the deposition chamber must be adjusted according to the ion gun specifications. This may involve reducing the pressure below the preferred pressures for deposition in the absence of an ion source.

The laser deposition method and system according to the present invention has numerous advantages over prior methods and systems, and the articles formed by the method according to the present invention have numerous advantages over the prior articles. For example, the method according to the present invention can be conducted at room temperature, if desired, thereby avoiding problems associated with oxidation of the substrate, degradation of the substrate or the film due to annealing and elimination of structural water, e.g., from hydroxylapatite. Also, the method according to the present invention can be conducted in a wide variety of gaseous environments, including water vapor environments. This feature lends a degree of control over the stoichiometry of the films. Operational parameters can be selected so as to (1) control whether a deposited film of biocompatible material is amorphous, crystalline, or a mixture of amorphous and crystalline phases, (2) control the crystal structure of the deposited film, (3) control the morphology of the deposited film, (4) achieve desired stoichiometry, e.g., the ratios of calcium to phosphorus in a deposited HA film and/or (5) provide better adhesion between the deposited film and the substrate. Moreover, for deposition of HA, operational parameters can be selected so as to control how much calcium phosphate (tricalcium phosphate or tetracalcium phosphate) is in a crystalline phase. Those operational parameters include the chemical makeup of the environment within the chamber, the pressure within the chamber and the temperature at the surface of the substrate. In addition, by selecting laser conditions (e.g., energy density, wavelength, pulse rate), target fabrication procedures (e.g., composition, density, sintering temperature) and/or by using ion beam assisted pulsed laser deposition, one can control the porosity of the deposited film and enhance the adhesion of the film to the substrate.

The following Examples demonstrate applications of the present invention. The Examples also show how operational parameters can be controlled, and how those parameters can be selected so as to achieve specific desired characteristics in the finished products.

EXAMPLE 1

Using a system as shown in FIG. 1, films of hydroxylapatite were deposited by pulsed laser deposition on flat, planar, polycrystalline Ti-6Al-4V substrates heated to various temperatures (as set forth in Table 1) in a chamber environment of argon/water at a total pressure of 300 mTorr. The phases (determined in Example 1, as in Examples 2 and 5, by X-ray diffraction) of the resulting deposited films are set forth in Table 1, in which "ph" designates tetracalcium phosphate.

TABLE 1

| Experiment | Chamber Environment | Temperature (°C.) | Phase(s) |
|---|---|---|---|
| 1 | argon/water, 300 mTorr | 30 | amorphous |
| 2 | argon/water, 300 mTorr | 30 | amorphous |
| 3 | argon/water, 300 mTorr | 200 | amorphous |
| 4 | argon/water, 300 mTorr | 200 | amorphous |
| 5 | argon/water, 300 mTorr | 400 | amorphous |
| 6 | argon/water, 300 mTorr | 400 | amorphous + HA |
| 7 | argon/water, | 400 | amorphous + HA |

TABLE 1-continued

| Experiment | Chamber Environment | Temperature (°C.) | Phase(s) |
|---|---|---|---|
| 8 | argon/water, 300 mTorr | 400 | amorphous + HA |
| 9 | argon/water, 300 mTorr | 400 | amorphous + HA |
| 10 | argon/water, 300 mTorr | 400 | HA |
| 11 | argon/water, 300 mTorr | 400 | HA |
| 12 | argon/water, 300 mTorr | 400 | HA |
| 13 | argon/water, 300 mTorr | 400 | HA |
| 14 | argon/water, 300 mTorr | 400 | HA |
| 15 | argon/water, 300 mTorr | 500 | amorphous + HA |
| 16 | argon/water, 300 mTorr | 500 | amorphous + HA |
| 17 | argon/water, 300 mTorr | 500 | amorphous + HA |
| 18 | argon/water, 300 mTorr | 500 | amorphous + HA |
| 19 | argon/water, 300 mTorr | 500 | amorphous + HA |
| 20 | argon/water, 300 mTorr | 500 | HA |
| 21 | argon/water, 300 mTorr | 500 | HA + ph |
| 22 | argon/water, 300 mTorr | 500 | amorphous + HA + ph |
| 23 | argon/water, 300 mTorr | 500 | amorphous + HA + ph |
| 24 | argon/water, 300 mTorr | 600 | HA |
| 25 | argon/water, 300 mTorr | 700 | HA + ph |
| 26 | argon/water, 300 mTorr | 800 | HA |
| 27 | argon/water, 300 mTorr | 800 | HA + ph |

EXAMPLE 2

Figure 3:
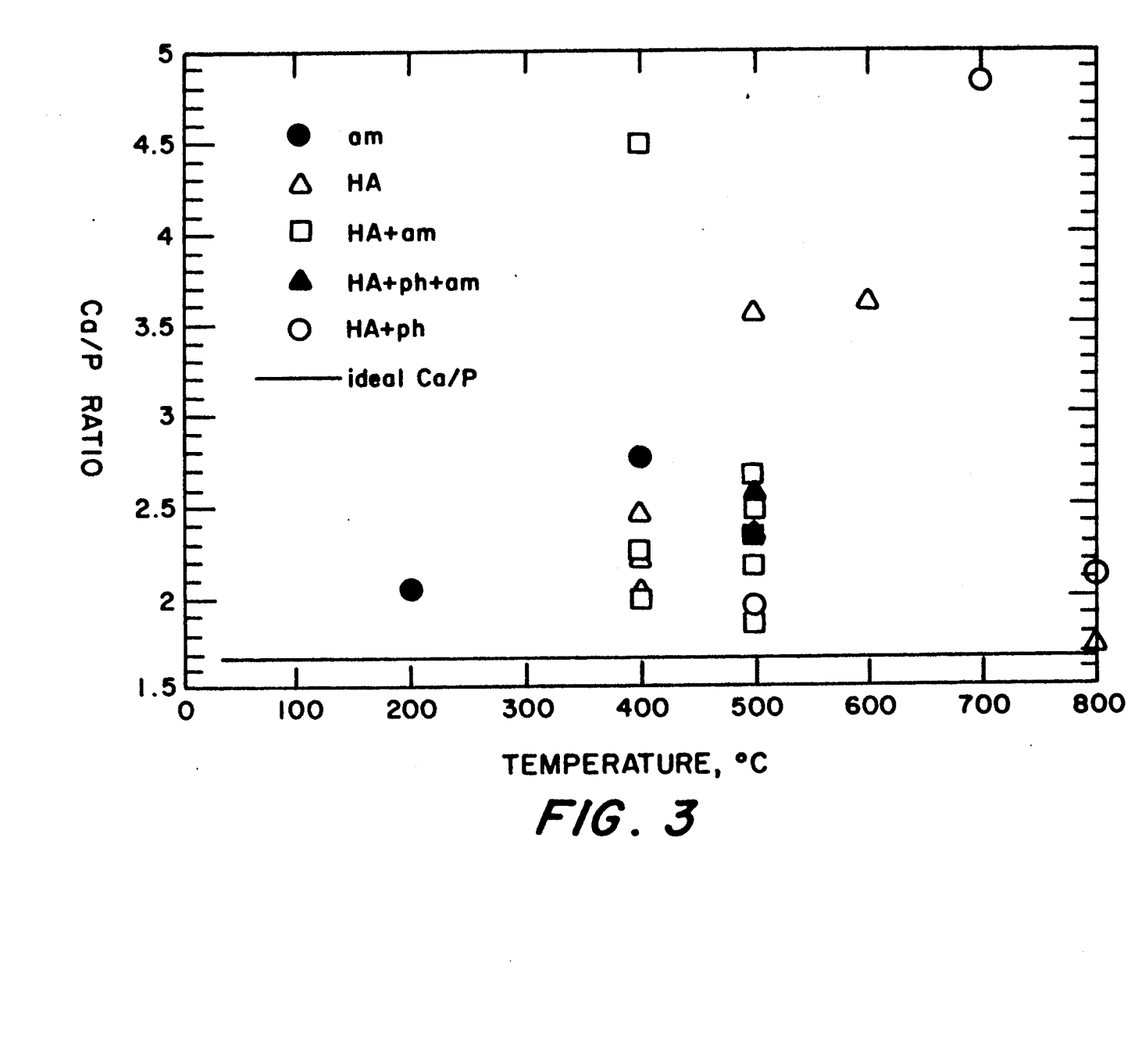
FIGS. 3, 4 and 5 are graphs of Ca/P ratios of films deposited in Examples 2, 3 and 4 (below), respectively.

Again using a system as shown in FIG. 1, films of hydroxylapatite were deposited by pulsed laser deposition on Ti-6Al-4V substrates heated to various temperatures (as shown in FIG. 3) in a chamber environment of argon/water at a total pressure of 300 mTorr. The Ca/P ratios (determined in this Example, as in Examples 3–5, by Rutherford Backscattering Spectrometry) for the deposited films and the phase(s) in those films are depicted in FIG. 3 (in which "am" designates amorphous and "ph" designates crystalline tetracalcium phosphate).

EXAMPLE 3

Figure 4:
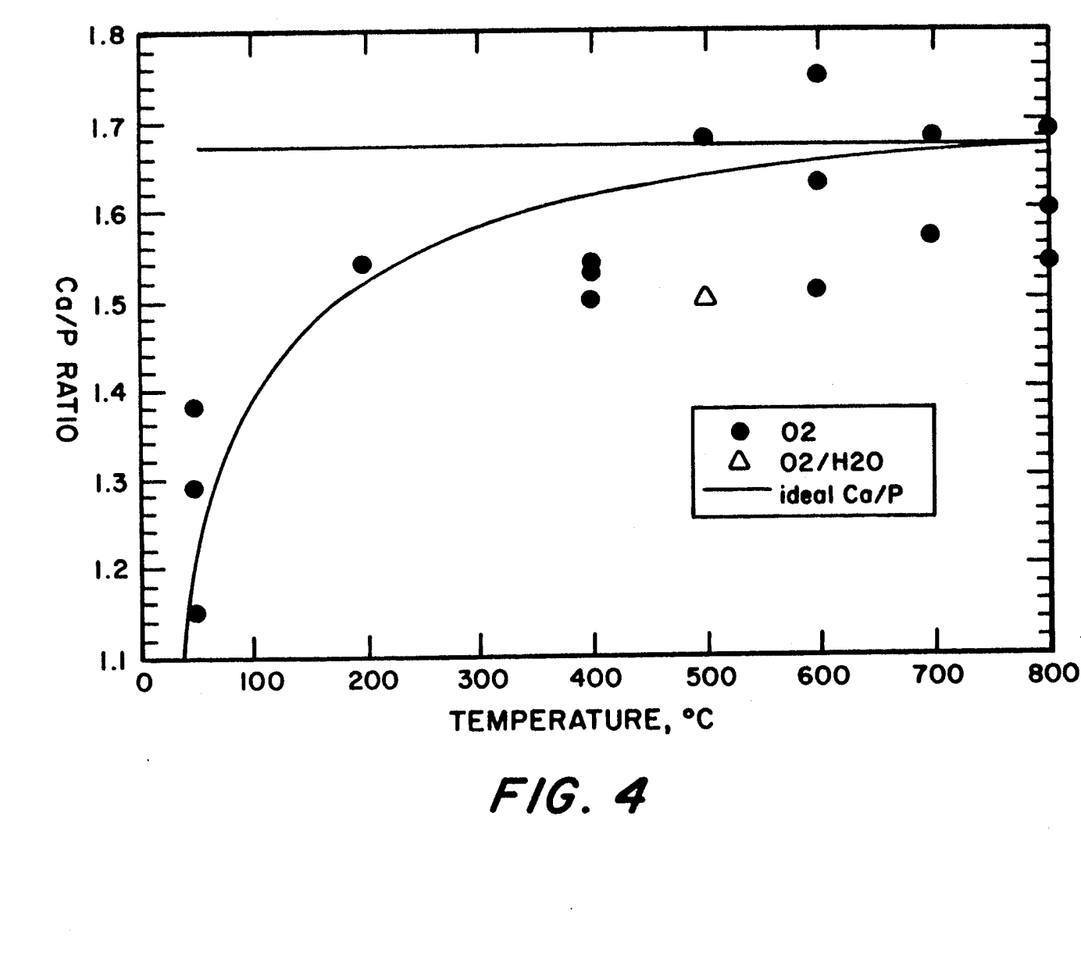

Again using a system as shown in FIG. 1, films of hydroxylapatite were deposited by pulsed laser deposition on Ti-6Al-4V substrates heated to various temperatures (indicated in FIG. 4) in chamber environments of oxygen (not using a bubbler 20 as shown in FIG. 1) or oxygen/water (indicated in FIG. 4) at a pressure of 300 mTorr. The Ca/P ratios for the deposited films are depicted in FIG. 4.

EXAMPLE 4

Figure 5:
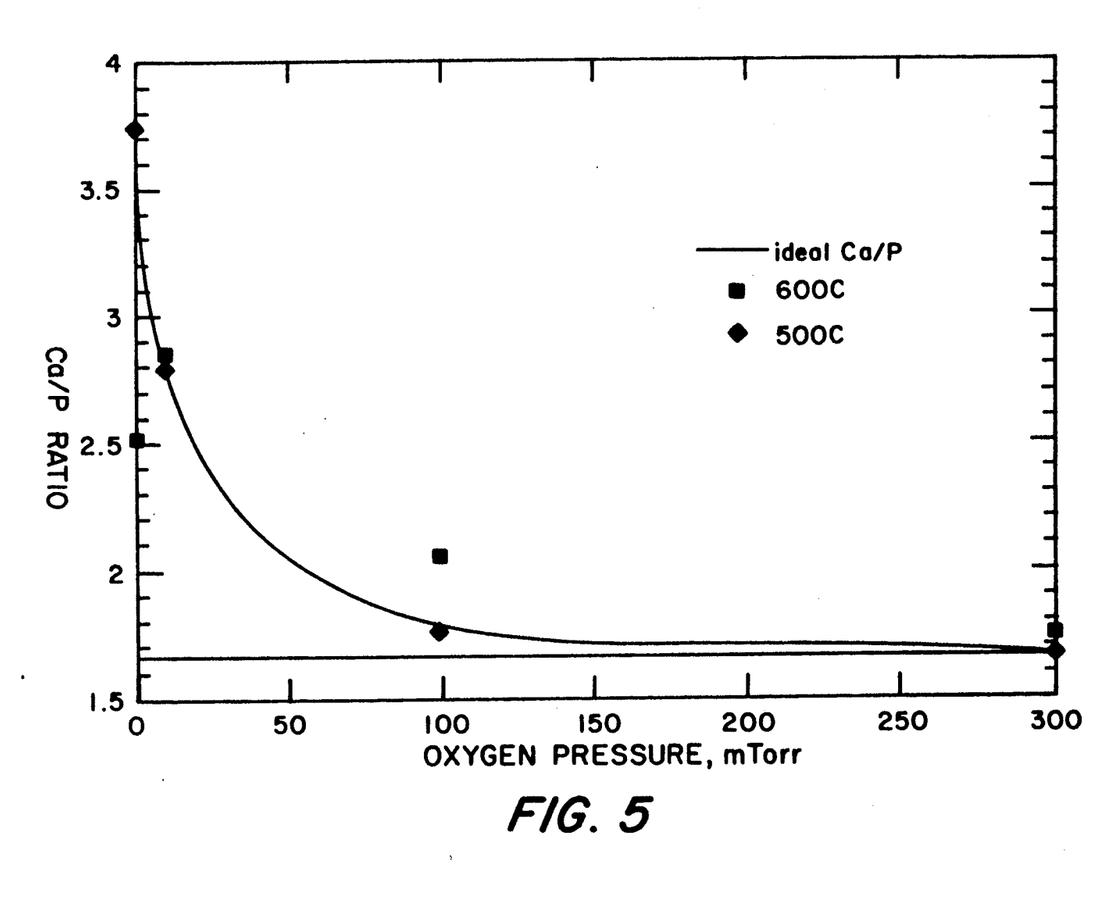

Using a system as shown in FIG. 1 (except that it did not include the bubbler 20), films of hydroxylapatite were deposited by 21 pulsed laser deposition on Ti-6Al-4V substrates heated to 500° C. or 600° C. (as shown in FIG. 5) in a chamber environment of oxygen at various total pressures (as shown in FIG. 5). The Ca/P ratios for the deposited films are depicted in FIG. 5.

EXAMPLE 5

Again using a system as shown in FIG. 1 (except that it did not include the bubbler 20), films of hydroxylapatite were deposited on Ti-6Al-4V substrates by pulsed laser deposition under temperature and pressure conditions as set forth in Table 2. the Ca/P ratios and the crystal structure and phases of the resulting articles are also shown in Table 2.

TABLE 2

| Temperature, °C. | Oxygen Pressure, mTorr | Ca/P ratio | Phase(s)* |
|---|---|---|---|
| 50 | 300 | 1.38 | — |
| 400 | 300 | 1.5 | amorphous |
| 600 | 300 | 1.75 | HA, (α-TCP) |
| 800 | 300 | 1.6 | α-TCP, (HA) |
| 600 | 100 | 2.05 | — |
| 600 | 10 | 2.85 | — |
| 600 | 0 | 2.52 | amorphous |

*The phase in smaller concentration is denoted by parenthesis.
α-TCP designates α-tricalcium phosphate.

EXAMPLE 6

Using a system as shown in FIG. 1 (which had a bubbler in those experiments in which the environment included water), films of hydroxylapatite were deposited by pulsed laser deposition on MgO<100>, silastic, and Si<111> substrates (as identified in Table 3 below at temperatures and in environments as identified in Table 3. The Ca/P ratios for the deposited films are listed in Table 3, in which "ph" designates crystalline tetracalcium phosphate.

TABLE 3

| Substrate | Temperature °C. | Environment | Phase | Ca/P Ratio |
|---|---|---|---|---|
| MgO<100> | 30 | 300 mTorr $O_2$ | amorphous | |
| MgO<100> | 600 | 300 mTorr $O_2$ | α-tricalcium phosphate + HA | |
| MgO<100> | 800 | 300 mTorr $O_2$ | HA + ph | |
| Silastic | 30 | 300 mTorr Ar/$H_2O$ | amorphous | 1.23 |
| Silastic | 30 | 300 mTorr Ar/$H_2O$ | amorphous | 0.95 |
| Silastic | 250 | 300 mTorr Ar/$H_2O$ | amorphous | 1.08 |
| Si<111> | 400 | 300 mTorr Ar/$H_2O$ | HA | 2.66 |
| Si<111> | 400 | 300 mTorr Ar/$H_2O$ | HA | 1.08 |

From the above and other Examples, the present inventors drew a number of conclusions as to general effects of various operational parameters on the resulting deposited film, as follow:

(1) to obtain pure crystalline HA films (i.e., with no amorphous hydroxylapatite and no tricalcium phosphate or tetracalcium phosphate) on Ti-6Al-4V or Si substrates, an argon/water chamber environment at a pressure of 300 mTorr and a temperature in the range of from about 400° C. to about 600° C. is preferred;

(2) in an argon/water chamber environment or an oxygen chamber environment at a total pressure of 300 mTorr, at temperatures below 400° C., the deposited films are generally amorphous, regardless of substrate;

(3) in an argon/water chamber environment, at temperatures greater than 600° C., at a total pressure of 300 mTorr, the deposited films on Ti-6Al-4V or Si frequently include tetracalcium phosphate and crystalline HA;

(4) in an oxygen chamber environment at a pressure of 300 mTorr, at temperatures between 400° C. and 700° C., the deposited films generally include crystalline HA and α-tricalcium phosphate, whereas at temperatures greater than 700° C., the deposited films generally include crystalline HA and β-tricalcium phosphate;

(5) in an oxygen chamber environment at a pressure of 300 mTorr, at temperatures below about 400° C., the deposited films are generally amorphous;

(6) in an oxygen chamber environment, at a pressure less than or equal to 100 mTorr and a temperature of 600° C., the deposited films are generally amorphous;

(7) in an oxygen chamber environment, the Ca/P ratio in deposited films tends to be higher at lower pressures;

(8) in an oxygen chamber environment at 300 mTorr, the Ca/P ratio in deposited films tends to be lower at lower temperatures;

(9) in an argon/water chamber environment, the Ca/P ratio in films deposited on Ti-6Al-4V or Si tends to be greater than the theoretical Ca/P ratio of HA;

(10) Ca/P ratios of films deposited at temperatures $\leq 250°$ C. in Ar/water at 300 mTorr on silastic substrates tend to be less than the theoretical Ca/P ratio of HA;

(11) presence of water vapor in the chamber environment generally enhances the likelihood of obtaining HA or the amount of HA;

(12) adhesion of deposited films to Ti-6Al-4V substrates tends to be better when deposited in an argon/water chamber environment than when deposited in an oxygen chamber environment; and (13) adhesion of deposited films to Ti-6Al-4V substrates tends to be better when deposited at a temperature below 600° C. than when deposited at a temperature above 600° C.

Although the methods, apparatuses and articles in accordance with the present invention have been described in connection with preferred embodiments, it will be appreciated by those skilled in the art that additions, modifications, substitutions and deletions not specifically described herein may be made without departing from the spirit and scope of the invention as defined in the appended claims.

What is claimed is:

1. A method for depositing biocompatible ceramic material comprising hydroxylapatite onto a substrate, the method including the steps of exposing biocompatible ceramic material comprising hydroxylapatite to a pulsed laser beam at a position adjacent to a surface of a substrate such that said biocompatible ceramic material is ablated off the target and deposited on said surface of said substrate, said surface of said substrate and said target being positioned within a chamber having a reactive gas environment comprising water vapor, and being in contact with said reactive gas environment.

2. A method as recited in claim 1, wherein said biocompatible material being exposed is being moved relative to said pulsed laser beam.

3. A method as recited in claim 1, wherein said laser beam is produced by a pulsed KrF excimer laser.

4. A method as recited in claim 1, wherein said substrate comprises at least one material selected from the group consisting of Ti alloys, MgO, Si, GaAs, InP, GeSi, SiC, synthetic rubbers, stainless steels, Co—Cr alloys, essentially pure Ti and $Al_2O_3$.

5. A method as recited in claim 4, wherein said substrate consists essentially of a material selected from the group consisting of Ti alloys, MgO, Si, GaAs, InP, GeSi, SiC, synthetic rubbers, stainless steels, Co—Cr alloys, essentially pure Ti and $Al_2O_3$.

6. A method as recited in claim 1, wherein said a surface of said biocompatible material, as it is being deposited on said substrate, is maintained at a temperature in the range of from about 20° C. to about 1200° C.

7. A method as recited in claim 6, wherein said reactive gas environment consists essentially of argon and water vapor.

8. A method as recited in claim 7, wherein said chamber is maintained at a pressure of no more than about 400 mTorr.

9. A method as recited in claim 8, wherein said surface of said biocompatible material, as it is being deposited on said substrate, is maintained at a temperature of from about room temperature to about 800° C.

10. A method as recited in claim 9, wherein said surface of said biocompatible material, as it is being deposited on said substrate, is maintained at a temperature in the range of from about 400° C. to about 600° C.

11. A method as recited in claim 6, wherein said biocompatible material being exposed and said substrate are positioned within a chamber having an environment consisting essentially of oxygen gas and water vapor.

12. A method as recited in claim 11, wherein said chamber is maintained at a pressure of no more than about 400 mTorr.

13. A method as recited in claim 1, further comprising subjecting said substrate to an ion beam prior to depositing said biocompatible material onto said substrate.

14. The method of claim 1, wherein said chamber is maintained at a pressure of at least about 10 mTorr.

15. The method of claim 14, wherein said pressure is no more than about 400 mTorr.

16. The method of claim 1, wherein said substrate is a metallic element, a metallic alloy, a ceramic, or a polymer.

17. The method of claim 16, wherein said substrate is a metallic element or a metallic alloy.

18. A method as recited in claim 4, wherein said substrate comprises Ti-6Al-4V.

19. A method as recited in claim 18, wherein said substrate consists essentially of Ti-6Al-4V.

* * * * *